United States Patent [19]

Morand et al.

[11] Patent Number: 4,879,069

[45] Date of Patent: Nov. 7, 1989

[54] FLUORESCENT CONJUGATED POLYENE STEROL DERIVATIVES AS CELL MEMBRANE PROBES

[76] Inventors: Peter Morand, 4-274 Daly Avenue, Ottawa, Ontario, Canada, K1N 6G5; Jacinta Drew, Apt. 209-475 Elgin Street, Ottawa, Ontario, Canada, K2P 2E6; Arthur G. Szabo, 21 Beechmont Crescent, Gloucester, Ontario, Canada, K1B 4A7; Pierre R. Proulx, 57 Rebecca Crescent, Ottawa, Ontario, Canada, K1J 6C2

[21] Appl. No.: 867,565

[22] Filed: May 28, 1986

[30] Foreign Application Priority Data

May 31, 1985 [CA] Canada ................................. 482887

[51] Int. Cl.$^4$ ............................................. C07J 9/00
[52] U.S. Cl. ............................ 260/397.2; 260/397.4; 260/397.5
[58] Field of Search ....................... 260/397.2, 397.5; 514/182, 170

[56] References Cited

U.S. PATENT DOCUMENTS

| 4,464,298 | 8/1984 | Rappoldt et al. | 260/397.2 |
| 4,477,445 | 10/1984 | Philibert et al. | 260/397.2 |
| 4,680,290 | 7/1987 | Cassal et al. | 260/397.2 |

OTHER PUBLICATIONS

Alford et al., Chem. Physics Letters. Vol. 86, No. 3, (1982) "Florescence of DPH Derivatives evidence for emission from S2 and S1 excited state"
L. A. Chen et al., Biol. Chem., 1977, 252, 2163.
R. R. Rando et al., Biochim. Biophys., Acta, 1981, 684.
R. Bergeron et al., Anal. Biochem, 1982, 119, 12H.
F. Schroeder, FEBS Lett., 1981, 135, 127.
Y. J. Kao et al., Biochemistry, 1978, 17, 2689.
Y. Letourneaux et al., Chem., 1975, 40, 516.
A. O. Colonna et al., J. Steroid Biochem., 1973, 4, 171.
M. Cranney et al., Biochimica et Biophyica Acta, 735, (1983), 418–425.
F. Schroeder, Prog. Lipid Res., 1984, 23, 97.
T. A. Narwid et al., Helv. Chim. Acta, 1974, 57, 771.
J. P. Dusza et al., (to American Cynamid Co.), U.S. 3,351,638 (Cl. 260-397.1) Nov. 7, 1967, Appl. Jul. 29, 1966, (copy of Abstract enclosed).
G. R. Pettit et al., J. Org. Chem., 1970, 35, 1393.
J. Drew et al., J. Chem. Soc., 1985.

*Primary Examiner*—Cecilia Shen
*Attorney, Agent, or Firm*—Nixon & Vanderhye

[57] ABSTRACT

The present invention relates to the synthesis of conjugated polyene sterol derivatives, the compounds obtained and to their use as fluorescent probes for cellular membranes. The fluorescent probes of the present invention resemble cholesterol both structurally and in amphipathic nature. The probes of the present invention have potential for use in determining cholesterol levels and cholesterol properties and cell membrane properties and can be applied to clinical assays and diagnoses involving cholesterol.

7 Claims, 1 Drawing Sheet

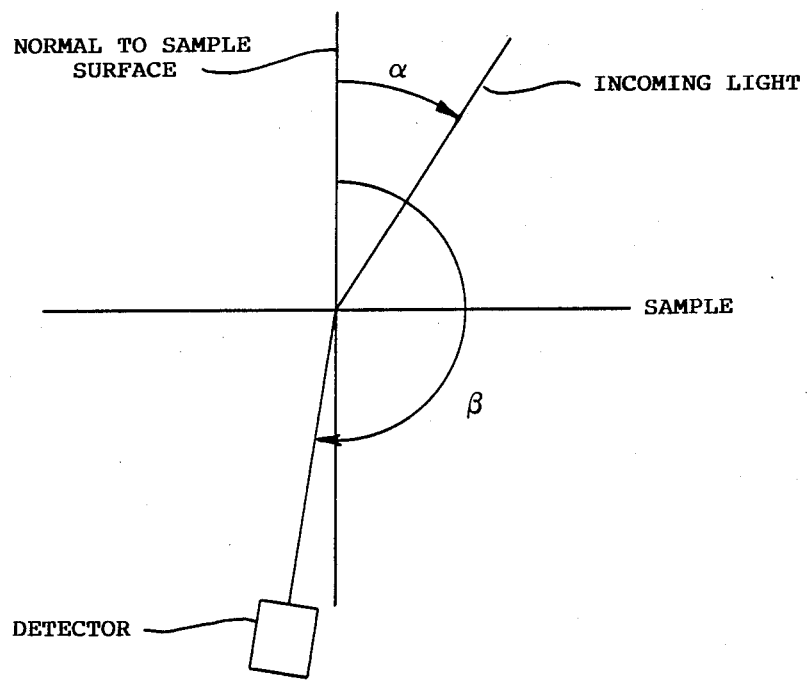

FLUORESCENT CONJUGATED POLYENE STEROL DERIVATIVES AS CELL MEMBRANE PROBES

BACKGROUND OF THE INVENTION AND PRIOR ART

The present invention relates to the synthesis of conjugated polyene sterol derivatives, the compounds obtained and to their use as fluorescent probes for cellular membranes.

A membrane probe is essentially a research tool used to probe (investigate) the environment of a membrane. Membrane probes find application, for example, in determining the effect of environmental pollutants and dietary constituents on cell membranes. Cell membranes are very selective and will permit only selected molecules to permeate the membrane. As well, the interactions between the membrane and its environment (i.e. the molecules in the environment) are very selective. Membrane probes are useful in the investigation of the structure and function of membrane constituents such as proteins and enzymes. Cholesterol is a major membrane constituent. The molecular structure of the probes of the present invention is very similar to cholesterol and thus the probes behave in a manner similar to cholesterol.

The probes of the present invention are fluorescent, so their behaviour in the membrane environment and their effect on the membrane can be easily determined by simply shining light on the membrane and observing the light emitted by the probe. Because of the very great sensitivity of fluorescence techniques, only very small amounts of extrinsic probe material need be incorporated into the sample of interest. This contrasts with other spectroscopic techniques such as nuclear magnetic resonance, absorption and electron spin resonance spectroscopy, which require significantly greater amounts of probe substance, with much greater risk of altering the system being investigated. Techniques using radio-isotopes have a high degree of sensitivity but by their nature are more hazardous and the radioisotopic probe materials have limited shelf life.

By studying the behiavour of the probe of the invention more can be learned about the behaviour of cholesterol. The probes of the present invention have potential for use in determining cholesterol levels and cholesterol properties in membranes and cell membrane properties and can be applied to clinical assays and diagnoses involving cholesterol.

Aromatic olefins, particularly diphenylhexatriene (DPH), have been used extensively as fluorescent probes of membrane fluidity, (see for example, L. A. Chen, R. E. Dale, S. Roth and L. Brand, J. Biol. Chem., 1977, 252, 2163). Such molecules, however, are not natural membrane constituents and can provide only indirect insight into protein-lipid and lipid-lipid interactions.

Cholesterol is an important lipid component, but its role in influencing membrane structure and dynamics is poorly understood. Some cholesterol-type molecules in which the C-3 alcohol function has been modified have been synthesized. (See for example, R. R. Rando, F. W. Bangerter and M. R. Alecio, Biochim. Biophys. Acta, 1981, 684, 12.) For example, the compounds Apart from a loss of the amphipathic nature of the cholesterol moiety in some of these derivatives (e.g. 1(a)), in all cases the C-3 hydroxy function has been drastically altered. Other membrane probes have been synthesized in which the C-3 hydroxy group is intact. (See for example, R. Bergeron and J. Scott, Anal. Biochem., 1982, 119, 12H; F. Schroeder, FEBS Lett., 1981, 1335, 127.) For example, the compounds -continued

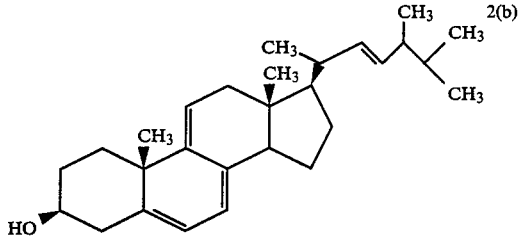

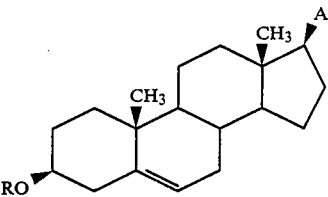

However, the unsaturation in the ring systems 2(a) and 2(b) drastically changes the molecular geometry. Such probes would be expected to pack differently from cholesterol in membranes and the lipid-probe interactions would be different from those of lipid-cholesterol.

Fluorescent chromophores in the C-17 side-chain of cholesterol have been reported. (See for example, Y. J. Kao, A. K. Soutar, K. -Y. Hong, H. J. Pownall and L. C. Smith, Biochemistry, 1978, 17, 2689.) For example, the compounds

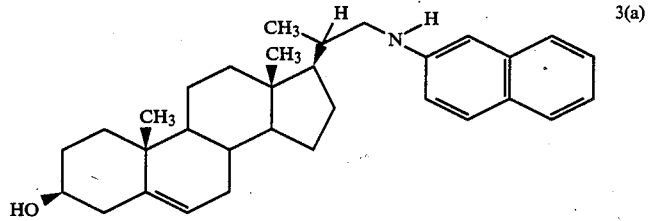

3(a)

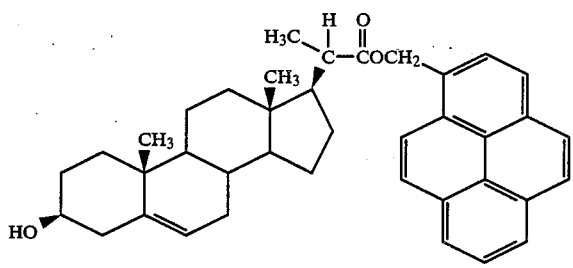

3(b)

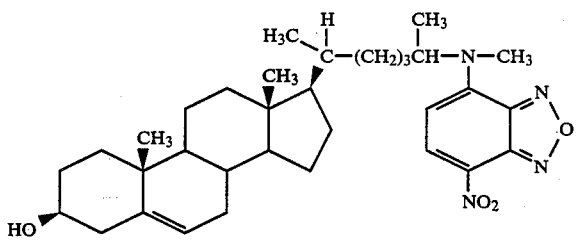

3(c)

In compounds of structures 3(a), 3(b) and 3(c) the hydrophobic character of the C-17 side-chain is much different from that of cholesterol. The membrane probes of the present invention, which have an olefinic fluorescent chromophore in the C-17 side-chain, resemble cholesterol more closely both in geometry and in amphipathic nature.

SUMMARY OF THE INVENTION

The present invention is directed to olefinic sterol derivatives of the formula I wherein
R represents H or an acy group suitable for use in cholesterol esterase assays, for example, a formyl, $C_2$–$C_{20}$ alkylcarbonyl, $C_3$–$C_{20}$ alkenylcarbonyl or $C_3$–$C_{20}$ alkynylcarbonyl group or an arylcarbonyl group and
A represents

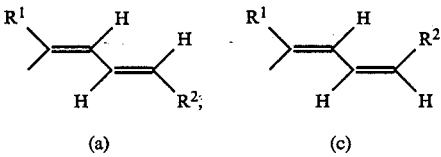

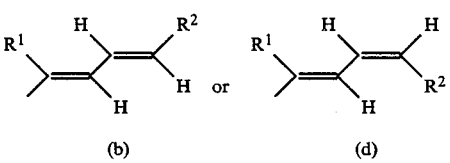

in which
$R^1$ represents H, $C_1$–$C_4$ lower alkyl, $C_2$–$C_4$ lower alkenyl, $C_2$–$C_4$ lower alkynyl or aryl, preferably phenyl or substituted phenyl wherein the substituent is consistent with fluorescence and $R^2$ represents —(CH=CH)$_n$—CH=CH$_2$, (CH=CH)$_n$-phenyl, —(CH=CH)$_n$-naphthyl, —(CH=CH)$_n$-tricyclic aryl —(CH=CH)$_n$-tetracyclic aryl or

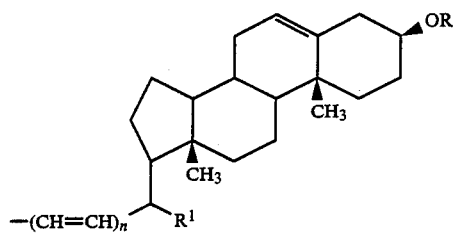

in which n is 0 to 3 and

R and $R^1$ are as defined above.

When $R^1$ is substituted phenyl, the substituents must be consistent with fluorescence. By a substituent which is consistent with fluorescence we mean a substituent which may enhance fluorescence, for example fluorine, chlorine or an aryl group, preferably phenyl, or a substituent which will not detract from fluorescence, for example lower alkyl such as methyl or ethyl.

Tricyclic aryl groups which can be present as part of the $R^2$ moiety incude anthracene and phenanthrene. Tetracyclic aryl groups which can be present as part of the $R^2$ moiety include naphthacene, 1,2-benzanthracene, chrysene and pyrene.

Specifically, the compounds of the present invention can be represented by the following structures:

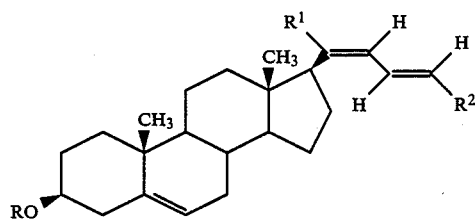
Ia

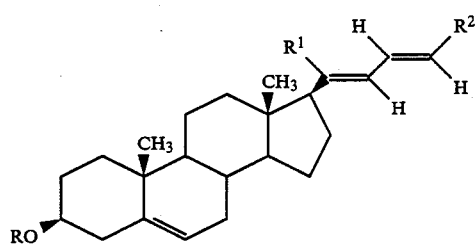
Ib

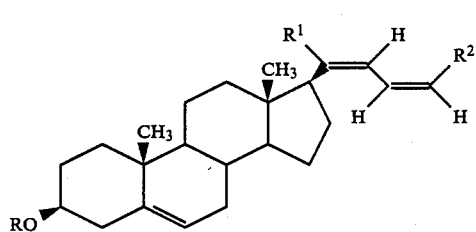
Ic

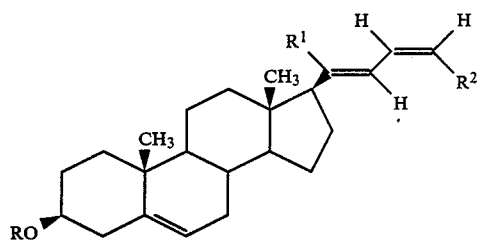
Id wherein

R, $R^1$, $R^2$ and n are as defined above.

Structures of formulae Ia, Ib and Id are preferred. Particularly preferred are structures of formulae Ia and Ib.

Of particular interest are the compounds obtained when $R^1$ is methyl and $R^2$ is —(CH=CH)-phenyl, when $R^1$ is phenyl and $R^2$ is —(CH=CH)-phenyl, when $R^1$ is methyl and $R^2$ is naphthyl and when $R^1$ is methyl and $R^2$ is phenyl.

The compounds of the present invention can be prepared by reacting a compound of formula II

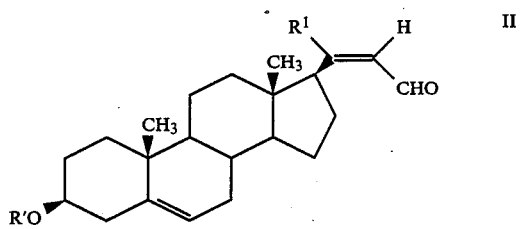
II or its isomer of formula II′

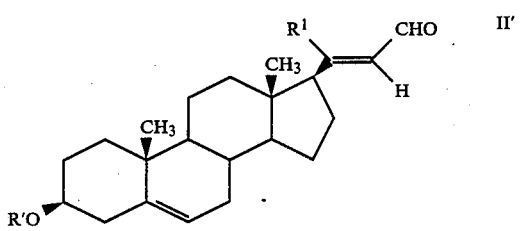
II′ in which

R′ is R as defined above or a protecting group and $R^1$ is as defined above with a base and a triphenylphosphonium compound of the formula

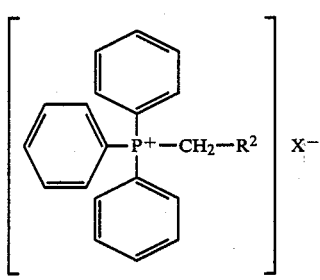

or a phosphonate compound of the formula

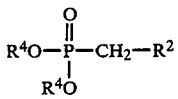

in which

R[2] is as defined above,

R[4] is a $C_1$-$C_4$ lower alkyl group and

X[-] is halide or other suitable nucleophilically displaceable group, and if required removing the protecting group.

It is preferred that R' is a protecting group. The preferred method of obtaining a compound of formula I in which R is acyl is to use a compound of formula II or II' in which R' is a protecting group, to deprotect to obtain a compound of formula I in which R is hydrogen and then to acylate to obtain a compound of formula I in which R is an acyl group. Acylation of cholesterol compounds at the 3-hydroxy position can be carried out by well known methods and usually proceeds in quantitative yield.

The protecting group must be a base stable group and is preferably a substituted silyl protecting group. Most preferably the protecting group is t-butyldimethylsilyl or t-butyl diphenylsilyl. The protecting group can be removed, for example, by reaction with tetrabutylammonium fluoride or acetic acid, water and tetrahydrofuran.

The base can be selected from the group consisting of, for example, n-butyllithium, lithium diisopropylamide, sodium hydride, lithium hydride, sodium methoxide, sodium ethoxide, sodium isopropoxide and potassium t-butoxide.

In a preferred feature R[4] is ethyl and X[-] is chloride or bromide.

The reaction between the compound of formula II or II' and the triphenylphosphonium compound can be carried out in tetrahydrofuran (THF) as solvent. When using a compound of formula II, if it is desired to increase the ratio of compound Ic to Ia in the product, there can be used as solvent a mixture of hexamethylphosphoramide (HMPA) and THF, suitably 10% HMPA and 90% THF. Similarly when using a compound of formula II' the ratio of compound Id to Ib in the product can be increased by using as solvent a mixture of HMPA and THF.

The compounds of formula II and II' can be prepared from a compound of formula IV

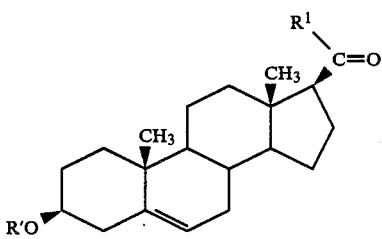

in which

R' and R[1] are as defined above. In one embodiment, the compound of formula IV is reacted with diethyl 2-(cyclohexylimino)vinyl phosphonate and the crude product hydrolysed, for example on a silica gel column to give the compounds of formulae II and II'. The diethyl 2-(cyclohexylimino)vinyl phosphonate can be obtained by hydrolysis of diethylphosphonoacetaldehydediethyl acetal and subsequent condensation with cyclohexylamine.

In an alternative embodiment the compound of formula IV is reacted with vinyl magnesium bromide with further hydrolysis to obtain a compound of formula III

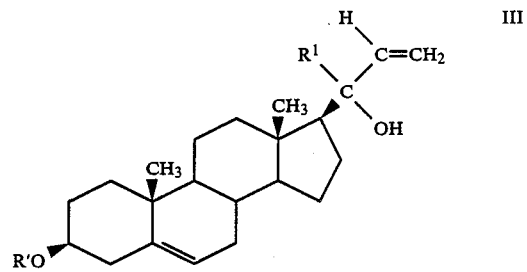

in which

R' and R[1] are as defined above.

The compound of formula III is then oxidatively rearranged.

In a preferred feature the oxidative rearrangement is carried out in methylene chloride in the presence of pyridinium chlorochromate, imidazole and sodium acetate which induce allylic rearrangement of the hydroxyl group and its oxidation to an aldehyde group.

The oxidative rearrangement can also be achieved by a first allylic rearrangement under mildly acidic conditions followed by oxidation with a mild oxidizing agent, for instance, manganese dioxide, Moffat's reagent or 2,3-dichloro-5,6-dicyanobenzoquinone.

The isomeric compounds of formula II and II' can be purified and separated into isomers by chromatography, preferably by column chromatography or by high performance liquid chromatography.

For a more direct method of obtaining compounds of formula I with configuration (b), the compound of formula IV (in which R' and R" are as defined above) is treated with a phosphonate compound of formula

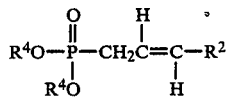

and a base. Suitable bases include those mentioned above. If R' is a protecting group, the protecting group must be a base stable group and is preferably a substituted silyl protecting group. Most preferably the protecting group is t-butyldimethylsilyl or t-butyldiphenylsilyl. The protecting group can be removed, for example, by reaction with tetrabutylammonium fluoride or acetic acid, water, and tetrahydrofuran.

The present invention is also directed to a method of analyzing cholesterol properties and cell membrane properties wherein a compound of formula I is admixed with a membrane sample and the compound-sample adduct is subjected to absorption or fluorescence spectroscopy. In one embodiment, the membrane sample is suspended in an aqueous medium, buffered, if necessary, to a pH between 6 and 8, preferably at physiological pH, which is 7.4. Examples of preferred buffers include phosphate buffer tris(hydroxymethyl)amino methane hydrochloride (TRIS) and sodium cacodylate. To the suspended sample there is added a very small volume of solution of known concentration of the compound of formula I. Suitable solvents include methanol, ethanol, chloroform, acetone, dimethylsulfoxide and THF. The mixture is vortexed immediately, incubated at a suitable temperature, preferably 37° C., for a time sufficient to incorporate the compound of formula I in the membrane. The compound-sample mixture may or may not be subjected to sonication to help the incorporation. The supernatant liquid is removed and is subjected to absorption, fluorescence or polarized fluorescence spectroscopy.

In an alternative embodiment, an aqueous suspension of the membrane sample is added to a dried film of a compound of formula I on the inside of a round bottom flask. The obtained mixture is then vortexed and subjected to the other steps described above to incorporate the compound of formula I in the membrane. The supernatant is again removed and subjected to absorption, fluoresence or polarized fluorescence spectroscopy.

In fluorescence polarization spectroscopy, polarized light is directed at the sample under investigation, and measurements of the amount of fluorescent light from the sample polarized parallel and perpendicular to the incident polarization direction are taken. Measurement of either polarization, polarization ratio or anistropy can give information about the fluidity of the sample under investigation. For example, if the ratio of the intensities of parallel to perpendicular polarized light (polarization ratio), is 1 or close to 1, in the absence of instrumental and experimental artifacts such as monochromator polarization bias, then the probe molecule moves relatively freely in the membrane and the membrane is said to be fluid in the region of the probe. If the ratio is greater than 1 the movement of the probe molecule is more restricted in the membrane and the membrane is not as fluid in the region of the probe. Hence the probes of the invention permit measurements of cell membrane fluidity and therefore permit studies to determine what relationships may exist between fluidity of its membrane and other properties of a cell. Other membrane properties can also be determined. As well, because the probe molecule is very much like cholesterol the behaviour of the probe molecule can be useful in predicting how cholesterol will behave in a similar membrane environment. The probe molecule, which is detectable by virtue of its fluorescence, can be used as labelled cholesterol. For instance, half of all deaths in the United States are caused by atherosclerosis, the disease in which cholesterol, accumulating in the wall of arteries, forms bulky plaques that inhibit the flow of blood until a clot eventually forms, obstructing an artery and causing a heart attack or stroke. Labelled cholesterol, in the form of the probe molecules of this invention, can be used in the investigation of the process of atherosclerosis and its early diagnosis.

The present invention is also directed to a kit for determining cholesterol levels and cholesterol properties in membranes and cell membrane properties, which kit comprises a known concentration of the compound of formula I, a standard or blank, such as dimyristoyl phosphatidylcholine lipid or other lipids for vesicle or liposome preparation, and, if necessary, buffer solution.

The invention will be further illustrated by reference to the following Examples.

EXAMPLE 1

The t-butyldimethylsilyl ether ($R'=Si(CH_3)_2C(CH_3)_3$) of pregnenolone ($R^1=CH_3$) was treated with vinylmagnesium bromide to give a quantitative yield of a 90:10 mixture of epimeric C-20 alcohols of formula III (determined by integration of the 23-H peaks centred at $\delta$ 5.27 and 5.18; $\delta$ 5.09 and 5.00). Diastereoisomeric aldehydes of formulae II and II' were obtained in 88% yield by oxidative rearrangement of the epimeric alcohols with pyridinium chlorochromate, imidazole and sodium acetate in $CH_2Cl_2$ at room temperature for 20 hours. The E- and Z-aldehydes were assigned on the basis of their 21-$CH_3$ 300 MHz $^1$H n.m.r. resonances [in formula II' $R^1=CH_3$, $\delta$ (21-$CH_3$) 2.20; in formula II $R^1=CH_3$ $\delta$ (21-$CH_3$) 1.99] and were formed in an 80:20 ratio respectively [determined by integration of the 23-H peaks at $\delta$ 10.07 (E) and $\delta$ 9.97 (Z) and the 22-H peaks at $\delta$ 6.05 (Z) and $\delta$ 5.94 (E)]. Separation of the isomers was effected by reversed phase high performance liquid chromatography (Altex Ultrasphere* ODS 10 mm×25 cm column, 100% $CH_3CN$). The overall yield of 70% for the E-isomer of formula II' is an improvement over the methods uses previously for the analogous C-3 acetoxy E-isomer. (See Y. Letourneaux, M. M. L. Lo, N. Chaudhuri and M. Gut. J. Org. Chem. 1975, 40, 516 and A. O. Colonna and E. G. Gros, J. Steroid Biochem., 1973, 4, 171).

*Trade Mark

The E-aldehyde (in formula II' $R^1=CH_3$), was treated with E-cinnamyltriphenylphosphonium chloride and n-butyllithium in tetrahydrofuran giving a 75% yield of a mixture of conjugated trienes which were deprotected at C-3 with tetrabutylammonium fluoride. From $^1$H n.m.r. analysis ($^1$H-$^1$H correlated spectrum or COSY, coupling constants, integration and computer simulation in the olefinic proton region) the mixture of isomeric alcohols was assigned to a 39:61 ratio of the EEE [in formula Ib R=H, $R^1=CH_3$, $R^2=(CH=CH)$-phenyl] and the EZE [in formula Id R=H, $R^1=CH_3$, $R^2=(CH=CH)$-phenyl] trienes. The integration experiments focused on the 25-H signal of the EEE-isomer centred at $\delta$ 6.86 and the 6-H signal from both isomers at $\delta$ 5.34. Separation of these isomers was achieved by reversed-phase high performance liquid chromatography (Altex Ultrasphere* ODS 10 mm×25 cm column, 98:2 $CH_3CN:H_2O$). The characteristic n.m.r. signals for the olefinic protons in the side-chain of each of the isomers is given in Table 1.

TABLE 1

Chemical shifts and coupling constants of olefinic protons in the isomeric conjugated trienes [in formula Ib R=H, $R^1=CH_3$, $R^2=(CH=CH)$-phenyl and in formula Id R=H, $R^1=CH_3$, $R^2=(CH=CH)$-phenyl].

| | $\delta$ (J in Hz) | |
| --- | --- | --- |
| Proton | EEE isomer (in formula Ib R=H, $R^1=CH_3$, $R^2=$—(CH=CH)-phenyl) | EZE isomer (in formula Id R=H, $R^1=CH_3$, $R^2=$—(CH=CH)-phenyl) |
| 22 | 5.98 (11.3) | 6.45 (12.3) |
| 23 | 6.62 (11.3, 14.5) | 6.32 (11.2, 11.2) |
| 24 | 6.30 (14.6, 10.8) | 6.08 (11.1, 11.1) |
| 25 | 6.86 (10.8, 15.6) | 7.2–7.3 (under aromatic proton) |
| 26 | 6.49 (15.5) | 6.54 (15.4) |

The EEE-isomer isolated showed no detectable impurities and exhibited m.p. 171.5°–173° C.; $\lambda_{max}^{abs}$ 331 nm; 42000 dm$^3$ cm$^{-1}$ mol$^{-1}$ (methylcyclohexane); $\lambda_{max}^{fl}$ 390 nm ($\lambda^{ex}$, 330 nm, methylcyclohexane).

EXAMPLE 2

The procedure of example 1 was followed, except that the E aldehyde [in formula II', R'=Si(CH$_3$)$_2$C(CH$_3$)$_3$, R$^1$=CH$_3$] was treated with diethyl cinnamyl phosphonate and lithium diisopropylamide in tetrahydrofuran for 24 hours (−78° C.→room temperature). The resulting mixture of conjugated trienes was deprotected at C-3 with tetrabutylammonium fluoride. The EEE and EZE triene [Ib and Id respectively with R=H, R$^1$=CH$_3$, R$^2$=—CH=CH-phenyl] ratio was determined by high performance liquid chromatography to be 83:17 (Varian* SPC-18 column, 4 mm×15 cm, 2% H$_2$O, 98% CH$_3$CN, 330 nm). This procedure is thus more selected than the procedure of example 1 for synthesis of the EEE triene.
*Trade Mark The EEE & EZE trienes were separated by high performance liquid chromatography (Beckman Ultrasphere* ODS column 10 mm×25 cm, 98:2 CH$_3$CN: water, 330 nm). The EEE triene was dissolved in pyridine and heated (60° C.) with acetic anhydride for one hour to yield EEE triene 3β-acetate (in formula Ib R=CH$_3$CO, R$^1$=CH$_3$, R$^2$=—CH=CH-phenyl). The crude product obtained was a yellow oily liquid. Identification was made by mass spectrometry; m/z=484 g/mole (M+), m/z=424 g/mol (M+-CH$_3$CO$_2$H).
*Trade Mark

EXAMPLE 3

The procedure of example 1 was followed, except that the E aldehyde [in formula II', R'=Si(CH$_3$)$_2$C(CH$_3$)$_3$, R$^1$=CH$_3$] was treated with cinnamyl triophenylphosphonium chloride and n-butyllithium in tetrahydrofuran containing 10% of hexamethylphosphoramide for 24 hours (−78° C.→room temperature). The resulting mixture of trienes was deprotected at C-3 using tetrabutylammonium fluoride. The EEE and EZE triene [Ib and Id respectively with R=H, R$^1$=CH$_3$, R$^2$=—CH=CH-phenyl] ratio was determined by high performance liquid chromatography to be 1:99 (Varian* SPC-18 column, 4 mm×15 cm, 2% H$_2$O, 98% CH$_3$Cn, 330 nm). This method is the one of choice for synthesis of the EZE triene.
*Trade Mark

EXAMPLE 4

Compound Ib [R=H, R$^1$=CH$_3$, R$^2$=—(CH=CH)$_n$-phenyl where n=0] and Id [R=H, R$^1$=CH$_3$, R$^2$=—(CH=CH)$_n$-phenyl where n=0] have been synthesized. The aldehyde II' (R'=Si(CH$_3$)$_2$ C(CH$_3$)$_3$, R$^1$=CH$_3$] was treated with benzyltriphenylphosphonium bromide and n-butyllithium in tetrahydrofuran. The resulting 60/40 mixture of EZ/EE isomers were deprotected at C-3 with tetrabutylammonium fluoride in tetrahydrofuran. Identification of the mixture was made by 'H n.m.r. analysis and the chemical shifts are indicated in the Table 2 below.

TABLE 2

Chemical shifts of olefinic protons in the isomeric conjugated dienes [in formula Ib R=H, R$^1$=CH$_3$, R$^2$=(CH=CH)$_n$-phenyl where n = 0 and in formula Id R=H, R$^1$=CH$_3$, R$^2$=(CH=CH)$_n$-phenyl where n = 0]

| Proton | EE isomer δ (Ib, R=H, R$^1$=CH$_3$, R$^2$=phenyl) | EZ isomer δ (Id, R=H, R$^1$=CH$_3$, R$_2$=phenyl) |
|---|---|---|
| 22 | 6.36 | 6.09 |
| 23 | 7.11 | 7.22 |

TABLE 2-continued

Chemical shifts of olefinic protons in the isomeric conjugated dienes [in formula Ib R=H, R$^1$=CH$_3$, R$^2$=(CH=CH)$_n$-phenyl where n = 0 and in formula Id R=H, R$^1$=CH$_3$, R$^2$=(CH=CH)$_n$-phenyl where n = 0]

| Proton | EE isomer δ (Ib, R=H, R$^1$=CH$_3$, R$^2$=phenyl) | EZ isomer δ (Id, R=H, R$^1$=CH$_3$, R$_2$=phenyl) |
|---|---|---|
| 24 | 6.47 | 6.53 |

The mixture of dienes Ib and Id has an absorption maximum at 290 nm and a fluorescence maximum at 350 nm in methylcyclohexane.

EXAMPLE 5

The t-butyldimethyl silyl ether of pregnenolone (in formula (IV), R'=Si(CH$_3$)$_2$C(CH$_3$)$_3$, R$^1$=CH$_3$) was treated with diethyl cinnamyl phosphonate and n-BuLi in tetrahydrofuran for 24 hours (−78° C.→room temperature). Workup of the reaction product yielded a substance which showed one fluorescent spot (R$_f$=0.85, 19:1 hexane:ethyl acetate) by thin layer chromatography and a retention time of 50 minutes by high performance liquid chromatography (Beckman Ultrasphere* ODS, 10 mm×25 cm, 95% Methanol, 5% Hexane, 300 nm, 3 ml/min). The fluorescence spectrum of the HPLC purified product was measured in 19:1 methanol-hexane and found to have a fluorescence maximum at 350 nm and to be identical with that of the product of Example 4. The crude product formed was also determined to contain EE diene [in formula Ib, R'=Si(CH$_3$)$_2$C(CH$_3$)$_3$, R$^1$=CH$_3$, R$^2$=(CH=CH)$_n$-phenyl (where n=0)] by comparison of its 'H NMR spectrum with the data given in Table 2.
*Trade Mark

EXAMPLE 6

Diethylphosphonoacetaldehyde diethyl acetal was heated with an 8% solution of hydrochloric acid and a few crystals of hydroquinone at 75° C. for 16 hours. The reaction mixture was distilled to give pure formylmethylphosphonate (70°-72° C., 0.33 mm) which was then condensed with cyclohexylamine in methanol at 0° C. for 3 hours to give diethyl 2-(cyclohexylimino)vinyl phosphonate. The t-butyldimethylsilyl ether of pregnenolone [in formula IV, R'=Si(CH$_3$)$_2$C(CH$_3$)$_3$, R$^1$=CH$_3$] was treated with the above vinyl phosphonate and sodium hydride in tetrahydrofuran initially at 0° C. and then at reflux for 12 hours. The resulting reaction mixture was chromatographed on silica gel with hexane/ethyl acetate to give a mixture of the E-aldehyde [in formula II', R'=Si(CH$_3$)$_2$C(CH$_3$)$_3$, R$^1$=CH$_3$] and the Z-aldehyde [in formula II, R'=Si(CH$_3$)$_2$C(CH$_3$)$_3$, R$^1$=CH$_3$]. The ratio of aldehydes was determined by hig performance liquid chromatography to be E:Z as 96:4 (Varian* SPC-18 column, 4 mm×15 cm, 100% CH$_3$CN, 250 nm).
*Trade Mark The E-aldehyde was separated from its z isomer by high performance liquid chromatography (Serva* ODS 100 Polyol, 5 μm, 22 mm×50 cm, 100% MeOH, 254 nm) and then treated with diethyl 2-methylnaphthyl phosphonate and n-butyllithium in tetrahydrofuran for 24 hours (−78° C.→room temperature) to give a 55% yield of a mixture of the EE and EZ naphthyl dienes [Ib and Id respectively, with R=Si(CH$_3$)$_2$C(CH$_3$)$_3$, $R^1$=CH$_3$, $R^2$=naphthyl]. This mixture was deprotected at C-3-with tetrabutylammonium fluoride.
*Trade Mark The identity of the deprotected compounds was confirmed by mass spectroscopy, with an m/z value of 466 g mol$^{-1}$.

The ratio of EE to EZ naphthyldienes was determined by reversed phase high performance liquid chromatography (Beckman Ultrasphere* ODS Column, 10 mm×25 cm, 95% methanol, 5% water, λ=340 nm) to be 99:1. This ratio overstates the amount of EE isomer due to its higher extinction coefficient, i.e. greater absorption, at 340 nm. It is estimated that the ratio of EE:EZ isomers is at least 95:5.
*Trade Mark

FLUORESCENCE STUDIES OF LIPID VESICLES

The excited singlet state decay time (fluorescence lifetime) of the EEE triene Ib [R=H, $R^1$=CH$_3$, $R^2$=—CH=CH-phenyl] was determined to be 30+5 ps in free solution (tetrahydrofuran). Lifetime measurements at 20° C. of the EEE triene probe when incorporated in vesicles of the lipid dimyristoyl phosphatidyl choline (DMPC) [200 μl (2.5×10$^{-5}$M probe in THF). 250 μl (35 mg/ml of DMPC in CH$_3$Cl), 1.55 ml (20 mM tris-acetate buffer, pH 7.2); ratio of lipid to probe approximately 200:1] are shown in Table 3 below.

TABLE 3
Fluorescence lifetimes and fractional fluorescence of the EEE triene in DMPC vesicles.

| Percent Cholesterol | Lifetime, τ Fraction, F | |
|---|---|---|
| 0% | τ$_1$ = 0.93 ns, | τ$_2$ = 0.26 ns |
| | F$_1$ = 0.66, | F$_2$ = 0.34 |
| 10% | τ$_1$ = 1.22 ns, | τ$_2$ = 0.31 ns |
| | F$_1$ = 0.47, | F$_2$ = 0.53 |

Steady state fluorescence polarization and anisotropy measurements were made on the above vesicles in the gel phase (15° C.) and the liquid crystalline phase (30° C.). Results are given in Table 4.

TABLE 4
Steady state fluorescence and anisotropy values of the EEE triene in DMPC vesicles.

| Percent Cholesterol | 15° C. (Gel Phase) | 30° C. (Liquid Crystalline Phase) |
|---|---|---|
| 0% | (a) *2.03 | (a) 2.01 |
| | (b) 0.34 | (b) 0.34 |
| | (c) 0.255 | (c) 0.252 |
| 10% | (a) 1.54 | (a) 1.69 |
| | (b) 0.21 | (b) 0.26 |
| | (c) 0.15 | (c) 0.19 |

(*a) = Polarization Ratio,
(b) = Polarization,
(c) = Anisotropy

FLUORESCENCE STUDIES OF ORIENTED LIPID SAMPLES

A methanol solution (0.1 mM, 600 μl) of the EE triene Ib [R=H, $R^1$=CH$_3$, $R^2$=—CH=CH-phenyl] was mixed with egg phosphatidylcholine (15 mg; lipid to probe ratio approximately 250:1). After drying under nitrogen and then under vacuum for 24 hours, the sample was left in a dessicator in an atmosphere of water vapour (saturated solution of K$_2$SO$_4$ in water) for 12 hours at room temperature.

The resulting lipid-water mixture was applied to two microscope cover glasses which were slid over each other to assist in orienting the sample. The orientation was checked by looking for a uniform colour under a polarization microscope. After another 12 hours in the water vapour atmosphere and another check of the orientation, the two cover glasses were sealed with a two-component glue and blackened around the edges.

The same procedure was followed for a second sample except that 20% of the lipid component was cholesterol.

Steady-state fluorescence polarization measurements ($λ_{ex}$=330 nm, $λ_{em}$=380 nm, photon counting detection) of the two samples were made, varying the angles λ and β (see accompanying drawing):

α=0°, 10°, 20° ... 60°

β=130°, 140°, 150° ... 220° with β−α≥160°.

The results are shown in Tables 5 and 6.

TABLE 5
Steady-state fluorescence polarization of the EEE triene in oriented samples of egg phosphatidyl choline.

| α(°) | β(°) | Polarization Ratio (±0.01) | α(°) | β(°) | Polarization Ratio (±0.01) |
|---|---|---|---|---|---|
| 0 | 130 | 2.04 | 40 | 130 | 1.48 |
| | 140 | 2.19 | | 140 | 1.56 |
| | 150 | 2.33 | | 150 | 1.68 |
| | 160 | 2.45 | | 160 | 1.82 |
| | | | | 170 | 1.95 |
| 10 | 130 | 1.87 | | 180 | 2.06 |
| | 140 | 1.96 | | 190 | 2.16 |
| | 150 | 2.11 | | 200 | 2.26 |
| | 160 | 2.26 | | | |
| | 170 | 2.38 | 50 | 130 | 1.38 |
| | | | | 140 | 1.46 |
| 20 | 130 | 1.72 | | 150 | 1.57 |
| | 140 | 1.82 | | 160 | 1.70 |
| | 150 | 1.92 | | 170 | 1.87 |
| | 160 | 2.07 | | 180 | 2.08 |
| | 170 | 2.19 | | 190 | 2.15 |
| | 180 | 2.33 | | 200 | 2.21 |
| | | | | 210 | 2.27 |
| 30 | 130 | 1.59 | | | |
| | 140 | 1.68 | 60 | 130 | 1.33 |
| | 150 | 1.80 | | 140 | 1.41 |
| | 160 | 1.93 | | 150 | 1.49 |
| | 170 | 2.04 | | 160 | 1.63 |
| | 180 | 2.17 | | 170 | 1.81 |
| | 190 | 2.28 | | 180 | 2.02 |
| | | | | 190 | 2.27 |
| | | | | 200 | 2.27 |
| | | | | 210 | 2.26 |
| | | | | 220 | 2.30 |

TABLE 6
Steady-state fluorescence polarization of EEE triene in oriented samples of 80% egg phosphatidyl choline, 20% cholesterol

| α(°) | β(°) | Polarization Ratio (±0.005) | α(°) | β(°) | Polarization Ratio (±0.005) |
|---|---|---|---|---|---|
| 0 | 130 | 2.166 | 40 | 130 | 1.519 |
| | 140 | 2.214 | | 140 | 1.610 |
| | 150 | 2.276 | | 150 | 1.729 |
| | 160 | 2.282 | | 160 | 1.866 |
| | | | | 170 | 2.008 |
| 10 | 130 | 1.983 | | 180 | 2.149 |
| | 140 | 2.059 | | 190 | 2.267 |
| | 150 | 2.101 | | 200 | 2.416 |
| | 160 | 2.225 | | | |
| | 170 | 2.469 | 50 | 130 | 1.462 |
| | | | | 140 | 1.524 |
| 20 | 130 | 1.777 | | 150 | 1.642 |
| | 140 | 1.877 | | 160 | 1.770 |
| | 150 | 1.998 | | 170 | 1.923 |
| | 160 | 2.111 | | 180 | 2.068 |
| | 170 | 2.227 | | 190 | 2.211 |

TABLE 6-continued

Steady-state fluorescence polarization of EEE triene in oriented samples of 80% egg phosphatidyl choline, 20% cholesterol

| α(°) | β(°) | Polarization Ratio (±0.005) | α(°) | β(°) | Polarization Ratio (±0.005) |
|---|---|---|---|---|---|
| | 180 | 2.466 | | 200 | 2.330 |
| | | | | 210 | 2.452 |
| 30 | 130 | 1.635 | | | |
| | 140 | 1.725 | 60 | 130 | 1.405 |
| | 150 | 1.843 | | 140 | 1.485 |
| | 160 | 1.979 | | 150 | 1.596 |
| | 170 | 2.108 | | 160 | 1.729 |
| | 180 | 2.234 | | 170 | 1.859 |
| | 190 | 2.379 | | 180 | 2.003 |
| | | | | 190 | 2.144 |
| | | | | 200 | 2.270 |
| | | | | 210 | 2.403 |
| | | | | 220 | 2.528 |

Based on the assumption that the fluorescent side chain of the probe has cylindrical symmetry the data were analysed (C. Zannoni, A. Arcione and P. Cavatorta, Chem. Phys. Lipids, 1983 32 179) to give order parameters (maximum possible range 0 (low order)→1 (high order)) as shown below:

| % Cholesterol in sample | Order Parameter, S |
|---|---|
| 0 | 0.1 |
| 20 | 0.9 |

These results confirm that the probe reports on the fluidity and order of lipid systems. Further they suggest that the compound of the invention associates with the cholesterol domains in the sample. Hence the invention provides probes which can be used as "labelled cholesterol" in an environment with cholesterol molecules and that the "labelled cholesterol" will behave in a similar manner to cholesterol. The behaviour of cholesterol molecules in situ in membranes and their effect on the lipid order can be observed.

What we claim as our invention is:

1. An olefinic compound of formula I

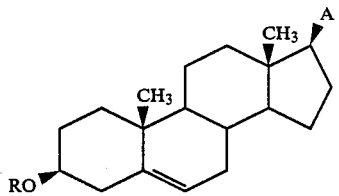

wherein R represents hydrogen, formyl, $C_2$–$C_{20}$ alkylcarbonyl, $C_3$–$C_{20}$ alkenylcarbonyl, $C_3$–$C_{20}$ alkynylcarbonyl or arylcarbonyl, and A represents

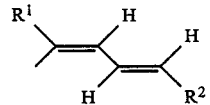 (a)

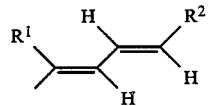 (b)

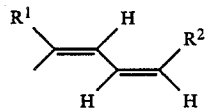 (c)

or

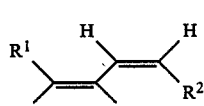 (d)

in which $R^1$ represents H, $C_1$–$C_4$ lower alkyl, $C_2$–$C_4$ lower alkenyl, $C_2$–$C_4$ lower alkynyl phenyl or phenyl substituted by a substituent selected from the group consisting of halo, aryl and lower alkyl and
$R^2$ represents —(CH=CH)$_n$—CH=CH$_2$, —(CH=CH)$_n$-phenyl, —(CH=CH)$_n$-naphthyl, —(CH=CH)$_n$-tricyclic aryl, —(CH=CH)$_n$-tetracylic aryl or

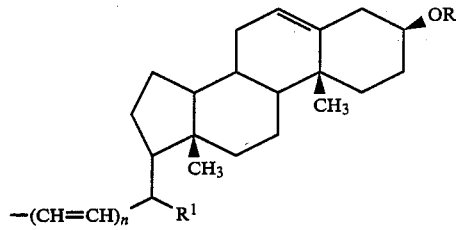

in which n is 0 to 3 and R and $R^1$ are as defined above.

2. A compound as claimed in claim 1, wherein $R^1$ is phenyl or phenyl substituted by a substituent selected from the group consisting of halo, aryl and lower alkyl.

3. A compound as claimed in claim 1 wherein R is hydrogen, $R^1$ is methyl, $R^2$ is phenyl and A has the configuration (a), (b) or (d).

4. A compound as claimed in claim 1 wherein R is hydrogen, $R^1$ is phenyl, $R^2$ is —(CH=CH)-phenyl and A has the configuration (a), (b) or (d).

5. A compound as claimed in claim 1 wherein $R^1$ is methyl, $R^2$ is naphthyl, R is hydrogen and A has the configuration (a), (b) or (d).

6. A compound as claimed in claim 1 wherein R is hydrogen, $R^1$ is methyl, $R^2$ is —(CH=CH)-phenyl and A has the configuration (a), (b) or (d).

7. A compound as claimed in claim 1 wherein R is acetyl, $R^1$ is methyl, $R^2$ is —(CH=CH)-phenyl and A has the configuration (a), (b) or (d).

* * * * *